US010441713B1

(12) United States Patent
Feldman et al.

(10) Patent No.: US 10,441,713 B1
(45) Date of Patent: Oct. 15, 2019

(54) ANESTHESIA INJECTION SYSTEM AND METHOD

(71) Applicants: Daniel Feldman, Farmington Hills, MI (US); Ilya Rozin, West Bloomfield, MI (US)

(72) Inventors: Daniel Feldman, Farmington Hills, MI (US); Ilya Rozin, West Bloomfield, MI (US)

(73) Assignee: Anestech, LLC, West Bloomfield, MI (US)

( * ) Notice: Subject to any disclaimer, the term of this patent is extended or adjusted under 35 U.S.C. 154(b) by 107 days.

(21) Appl. No.: 15/295,521

(22) Filed: Oct. 17, 2016

(51) Int. Cl.
*A61M 5/142* (2006.01)

(52) U.S. Cl.
CPC .................... *A61M 5/142* (2013.01)

(58) Field of Classification Search
CPC .. A61M 5/142; A61M 5/1414; A61M 5/1415; A61M 5/1417; A61M 5/1418; A61B 8/12
USPC ...................................... 128/DIG. 1
See application file for complete search history.

(56) References Cited

U.S. PATENT DOCUMENTS

| 2,715,900 | A | * | 8/1955 | Posner | H01H 23/16 |
| | | | | | 601/56 |
| 3,700,835 | A | * | 10/1972 | Rackson | H01H 9/0214 |
| | | | | | 200/505 |
| 4,504,200 | A | * | 3/1985 | Olson | F04B 43/1253 |
| | | | | | 417/476 |
| 4,955,772 | A | * | 9/1990 | Reck | F16B 37/041 |
| | | | | | 411/175 |
| 5,620,312 | A | * | 4/1997 | Hyman | A61M 5/142 |
| | | | | | 417/474 |
| 5,830,151 | A | | 11/1998 | Hadzic et al. | |
| 6,520,928 | B1 | | 2/2003 | Junior | |

(Continued)

FOREIGN PATENT DOCUMENTS

JP  2005-527334  9/2005

OTHER PUBLICATIONS

Webpage printout from CIVCO Medical Solutions showing "Reusable Ultrasound Needle Guide", Copyright 2016, CIVCO Medical Solutions, 2pgs.

(Continued)

*Primary Examiner* — Nathan R Price
*Assistant Examiner* — Tasnim Mehjabin Ahmed
(74) *Attorney, Agent, or Firm* — Tuggle Duggins P.A.; Blake P. Hurt

(57) ABSTRACT

An injection system for the independent administration of imaging-guided injections utilizing the hand-on-needle technique including a pressure-sensitive pump and a switch assembly is provided. The switch assembly is adjustably mounted to a probe with a releasable mount, and includes a displaceable lever that can be displaced from a neutral position to a first position to initiate an aspiration event at the needle and from a neutral position to a second position to initiate an injection event at the needle. The displaceable lever and the pressure-sensitive pump are in electronic communication with a control module, which includes programmable logic executed by a processor to send and receive electronic communication(s) from the pump and switch, including when to continue and/or terminate aspiration and injection events at the needle.

20 Claims, 5 Drawing Sheets

(56) References Cited

U.S. PATENT DOCUMENTS

| | | |
|---|---|---|
| 7,806,862 B2 | 10/2010 | Molnar |
| 9,044,542 B2 | 6/2015 | Patrick et al. |
| 2003/0167021 A1 | 9/2003 | Shimm |
| 2003/0225371 A1 | 12/2003 | Hadzic et al. |
| 2005/0006538 A1* | 1/2005 | Turi .................... A61M 5/1415 248/188.1 |
| 2006/0058738 A1* | 3/2006 | Ponzi .................... A61M 25/02 604/180 |
| 2009/0156926 A1* | 6/2009 | Messerly ............... A61B 5/042 600/409 |

OTHER PUBLICATIONS

Webpage printout from CIVCO Medical Solutions showing "In-Plane Ultrasound Needle Guide—Ultra-Pro II TM", Copyright 2016, CIVCO Medical Solutions, 4pgs.

Webpage printout from CIVCO Medical Solutions showing "Out-of-Plane Ultrasound Needle Guide—AccuSITE TM", Copyright 2016, CIVCO Medical Solutions, 4pgs.

* cited by examiner

ANESTHESIA INJECTION SYSTEM AND METHOD

FIELD OF THE INVENTION

The invention herein pertains to injection and/or aspiration systems and methods, and particularly pertains to an ergonomically designed injection controller that is mounted to an ultrasound probe which permits the independent administration of injectates.

DESCRIPTION OF THE PRIOR ART AND OBJECTIVES OF THE INVENTION

Physicians, clinicians, and other medical personnel often need to deliver a volume of anesthetic or other medication (e.g., steroid), other fluid and/or other material at or near (or aspirate fluid from) an anatomical location, such as, for example nerve tissue, a joint, an organ or the like. Accordingly, a needle can be inserted through a patient's skin and into the targeted location. A syringe or other fluid source that is in fluid communication with the needle can then be used to deliver the desired volume or other dosage of a medicament (e.g., anesthetic, medication, or the like), fluid and/or other material to the targeted anatomical location. One such type of injection that is being performed with increasing frequency in both inpatient and outpatient surgical settings particularly by anesthesiologists, is known as a peripheral nerve block. These injections have multiple benefits, including decreased anesthetic requirement and associated risks, decreased postoperative narcotic requirements and associated risks, improvement in postoperative pain, improvement in postoperative mental status, decreased nausea and improved bowel function during recovery, easier participation with physical therapy, and better overall patient satisfaction. Yet, one of many caveats to performing peripheral nerve blocks effectively is the requirement of two participants. Nearly all nerve block injections utilize ultrasound guidance, which is accomplished by first placing an ultrasound transducer (typically referred to as a "probe") over the target nerve to be blocked. Once the nerve is visualized on the ultrasound display monitor, the anesthesiologist inserts a needle under the ultrasound probe and observes it on the screen. Holding the ultrasound probe in one hand and the needle in the other, the anesthesiologist guides the needle tip towards the target nerve. The needle is connected through tubing to a syringe that an assistant holds. When the needle is adjacent to the target nerve, the anesthesiologist asks the assistant to aspirate (i.e. pull back on the syringe), confirms there is no blood in the tubing (indicating the needle tip is not in a blood vessel), and then asks the assistant to inject (push forward on the syringe), bathing the target nerve in local anesthetic.

As such, each patient requiring a peripheral nerve block procedure occupies the time and attention of two medical service providers. Another shortcoming of this current system is the anesthesiologist relies on what their assistant is "feeling" when they aspirate or inject. This information serves as data vital to the physician, as resistance when injecting may indicate an injection directly into the nerve (intraneural injection), a dangerous event that must always be avoided. Additionally, even if the anesthesiologist could "feel" the syringe resistance and/or even in the hands of an experienced assistant, this method is subjective and does not always predict and prevent intraneural injection.

Thus, in view of the problems and disadvantages associated with prior art systems and methods, the present invention was conceived and one of its objectives is to provide an injection system that can be efficiently and effectively utilized by a single medical service provider.

It is another objective of the present invention to provide an anesthesia injection system including a syringe pump and switch in communication via a control module.

It is still another objective of the present invention to provide an anesthesia injection system with a control switch mounted on an ultrasound probe.

It is yet another objective of the present invention to provide an anesthesia injection system with an adjustable switch mount that can accommodate a wide variety of ultrasound probe sizes and shapes.

It is a further objective of the present invention to provide an anesthesia injection system with a bidirectional, pressure-sensitive syringe pump to detect intravascular needle placement and prevent inadvertent intraneural injections.

It is still a further objective of the present invention to provide an anesthesia injection system with a control switch including a lever displaceable from a neutral position to a first position to initiate an aspiration event.

It is yet a further objective of the present invention to provide an anesthesia injection system with a control switch including a lever displaceable from a neutral position to a second position to initiate an injection event.

It is another objective of the present invention to provide an anesthesia injection system that is easy to operate and efficient to manufacture.

It is still another objective of the present invention to provide a method of injecting a patient with a medicament by providing an injection system with ultrasound guidance utilizing a single medical service provider.

It is yet another objective of the present invention to provide a method of injecting a patient with a medicament by displacing a lever of a control switch mounted on an ultrasound probe from a neutral position to a first position to initiate an aspiration event and from a neutral position to a second position to initiate an injection event.

Various other objectives and advantages of the present invention will become apparent to those skilled in the art as a more detailed description is set forth below.

SUMMARY OF THE INVENTION

The aforesaid and other objectives are realized by providing an injection system intended for use by anesthesiologists in the administration of specialized injection procedures such as nerve block injections, the injection system including a control module in electronic communication with a pressure-sensitive pump and a momentary control switch mounted on the exterior surface of an ultrasound probe. The pressure-sensitive pump is sized and shaped to receive a reservoir of medicament such as a syringe of fluid anesthetic and administer it out over a desired period of time at a predetermined rate. The pump also includes at least one sensor that can detect a change in pressure in the fluid connection between the reservoir of medicament, the needle that delivers the medicament to an anatomy of a patient, and any conduits, tubing, or the like that connect them. The control switch is adjustably mounted to the ultrasound probe with a releasable mount, and includes a displaceable lever that can be displaced from a neutral position to a first position to initiate an aspiration event at the needle and from a neutral position to a second position to initiate an injection event at the needle. The displaceable lever and the pressure-sensitive pump, including the at least one pressure sensor, are in electronic communication with the control module, which includes programmable logic executed by a processor to send and receive electronic communication(s) from the pump and switch, including when to initiate and terminate aspiration and injection events at the needle, whether executed by a user or determined based on information from the sensor and/or lever. A method utilizing the aforementioned injection system is also provided.

DETAILED DESCRIPTION OF THE PREFERRED EMBODIMENT AND OPERATION OF THE INVENTION

Figure 1:
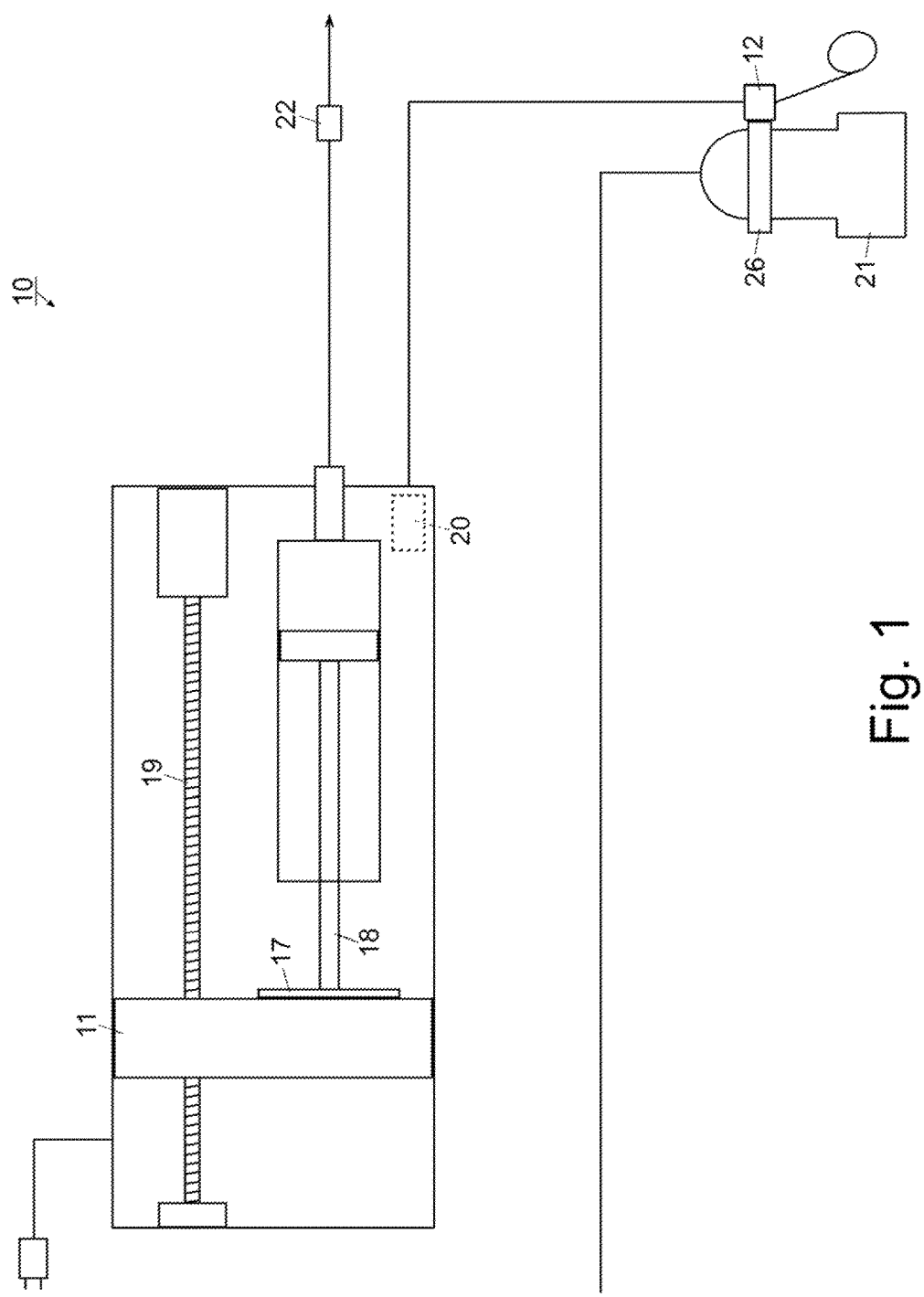
FIG. 1 shows a schematic representation of an injection system.
Figure 2:
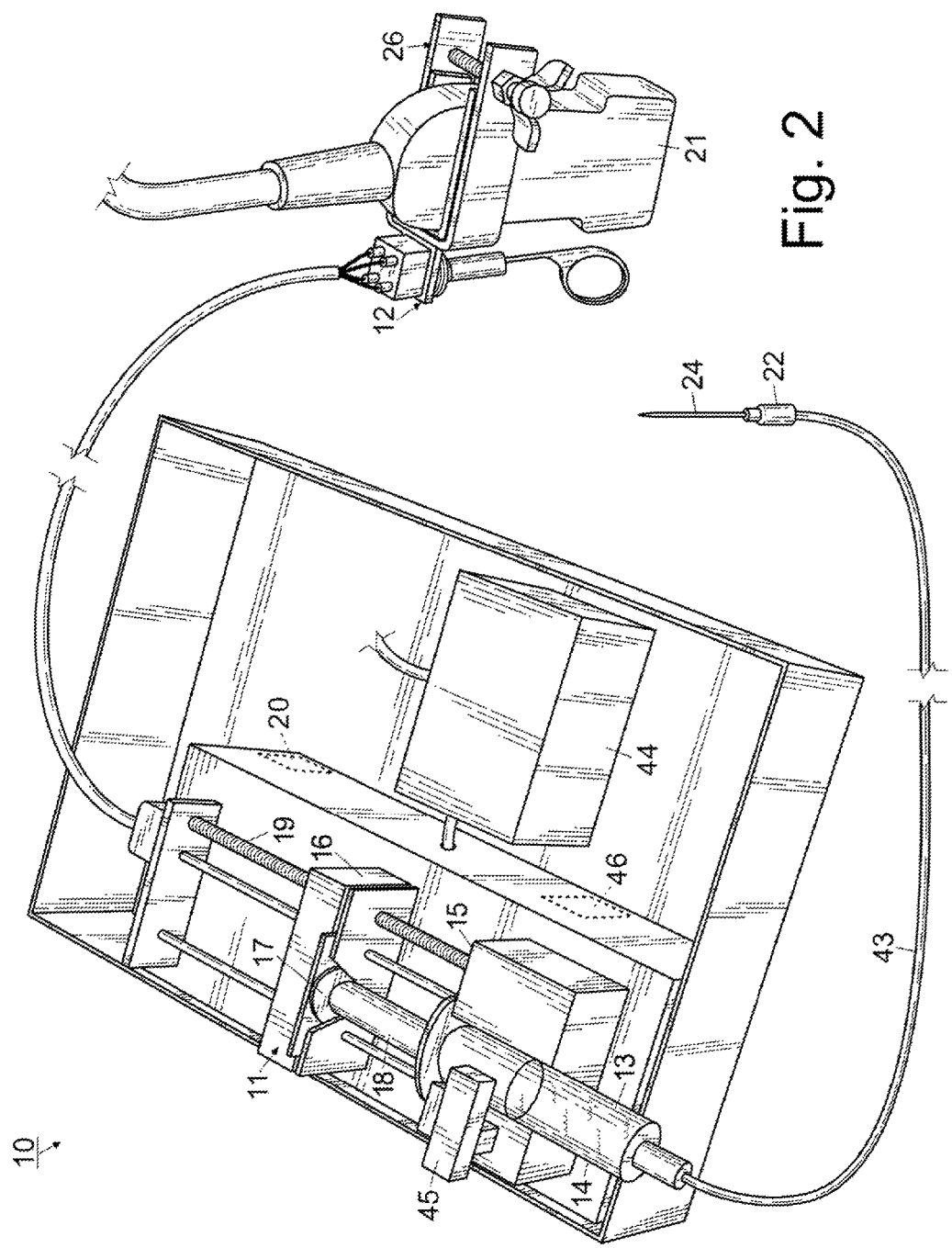
FIG. 2 pictures a perspective view of an injection system.

For a better understanding of the invention and its operation, turning now to the drawings, FIGS. 1-4B illustrate various views of preferred anesthesia injection system 10 that includes pump 11 in communication with switch assembly 12. In the preferred embodiment, pump 11 is a bidirectional pressure-sensitive pump sized and shaped to receive a reservoir of injectate such as medicament 14 such as syringe 13 containing fluid anesthetic that may be administered as a nerve block over a predetermined period of time and at a predetermined rate via tubing 43 affixed to needle hub 22 and needle 24. FIGS. 1 and 2 illustrate schematic and realistic renderings of an embodiment of this type of pump which is commercially available, but it should be understood that the specific make and model of the pump is not intended to be a limitation on the instant invention, as numerous variations exist that do not impact the novelty of the teachings contained herein. An embodiment of pump 11 is an electronic, screw-driven pump with rigid mount 15 that defines a channel of sufficient diameter to accommodate the receipt of a wide range of syringes and other fluid-dispensing members therein. Pump 11 also preferably includes receiver 16 sized and shaped to receive head 17 of syringe plunger 18 securely but releasably therein. Receiver 16 may be responsible for the displacement of plunger 18 fore and aft relative to the fixed position of syringe 13 at mount 15, for example by the mechanical engagement of a drive assembly (not shown) with elongated screw 19. Said drive assembly is in communication with system control module 20, demonstrated schematically in FIGS. 1 and 2 in dotted fashion, that receives instructions to compel the fore and aft (i.e. bidirectional) displacement of plunger 18 from switch assembly 12 as will be described in further detail below.

As is recognized in the art, imaging technology has become a vital component of targeting injection procedures such as nerve block injections, as medical personnel can detect and avoid the occurrence of an intraneural injection. The goal is to place needle 24 in close proximity to the nerve body (not shown) by manually guiding it via needle hub 22. Proper manipulation of probe 21 greatly aids in the aim of safe and effective injection procedure. While a common shape and style probe 21 is demonstrated in FIGS. 1-4B, it should be understood that this is but one embodiment of commercially available probes, and it is within the contemplation of the instant disclosure for mount 26 to be attached to a wide variety of transducer shapes and sizes. Probe 21 is typically connected to an imaging device such as an ultrasound machine including a monitor (not shown) which provides visual confirmation that needle 24 is in the appropriate position to commence injection/aspiration events. Further, switch assembly 12 is oriented relative to probe 21 throughout the figures in what may be referred to as "wide" grip configuration, whereby the width of the probe body spans the middle portion of the hand during use and lever 36 may be engaged by the thumb. An alternate configuration (not shown) that is similarly contemplated within the scope of this disclosure may be referred to as a "narrow" grip configuration, in that switch assembly 12 is rotated 90° relative to the wide grip orientation of probe 21.

Figure 3:
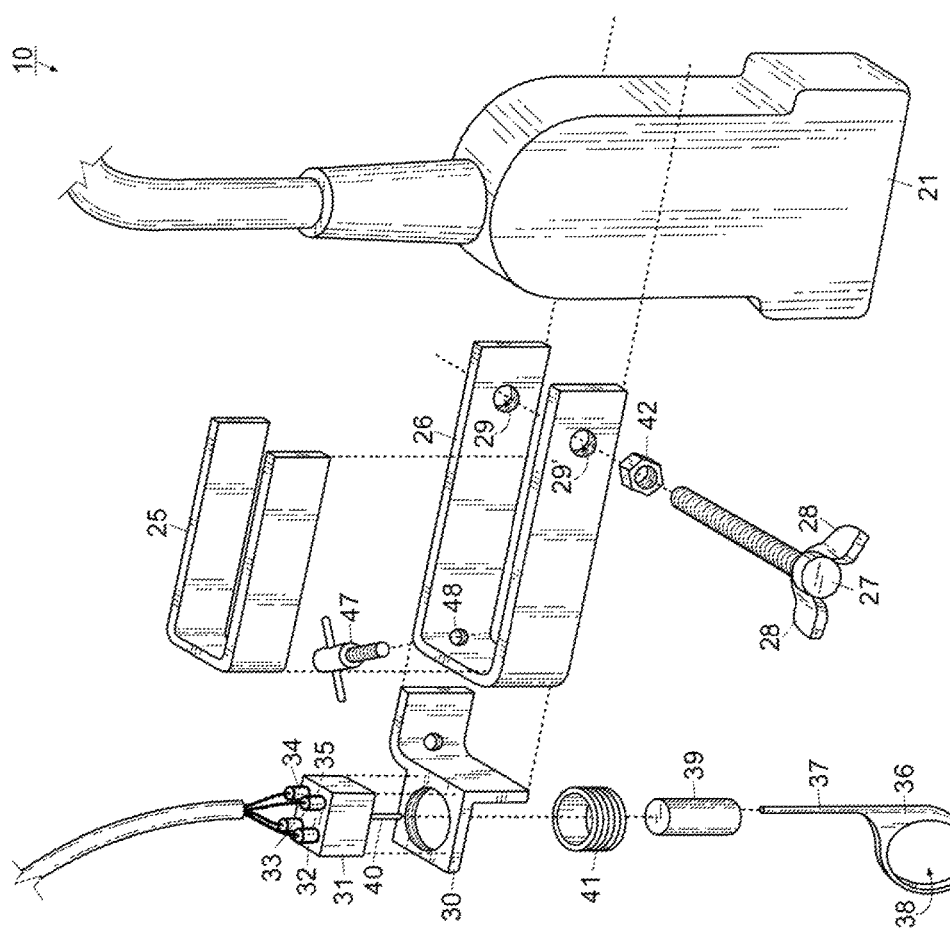
FIG. 3 depicts a perspective view of a mount of the injection system of FIG. 2 with various components exploded therefrom.
Figure 4:
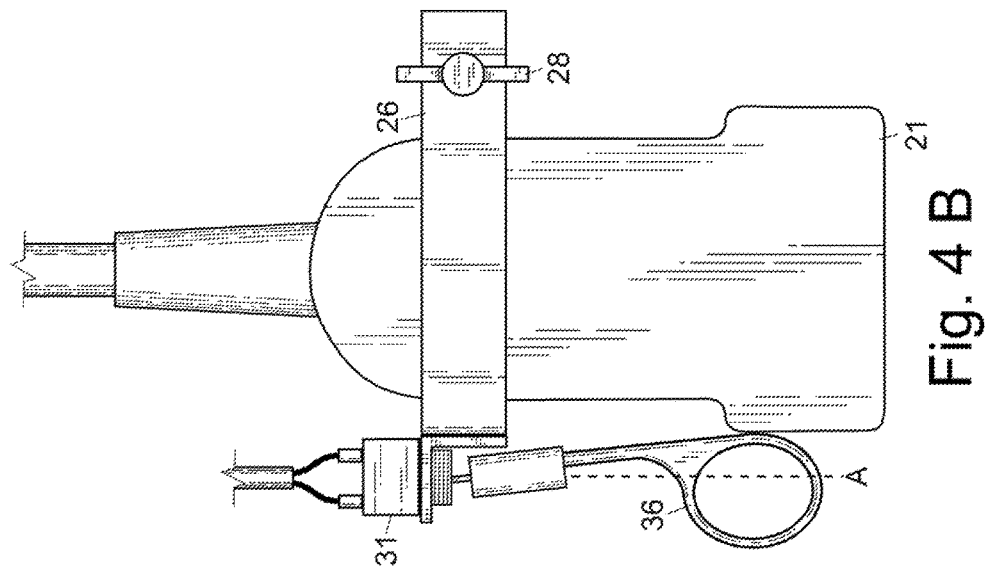
FIG. 4A demonstrates an elevated side view of the switch of the injection system of FIG. 2 with a displaceable lever in a first position.
FIG. 4B illustrates an elevated side view of the switch of the injection system of FIG. 2 with a displaceable lever in a second position.
Figure 4:
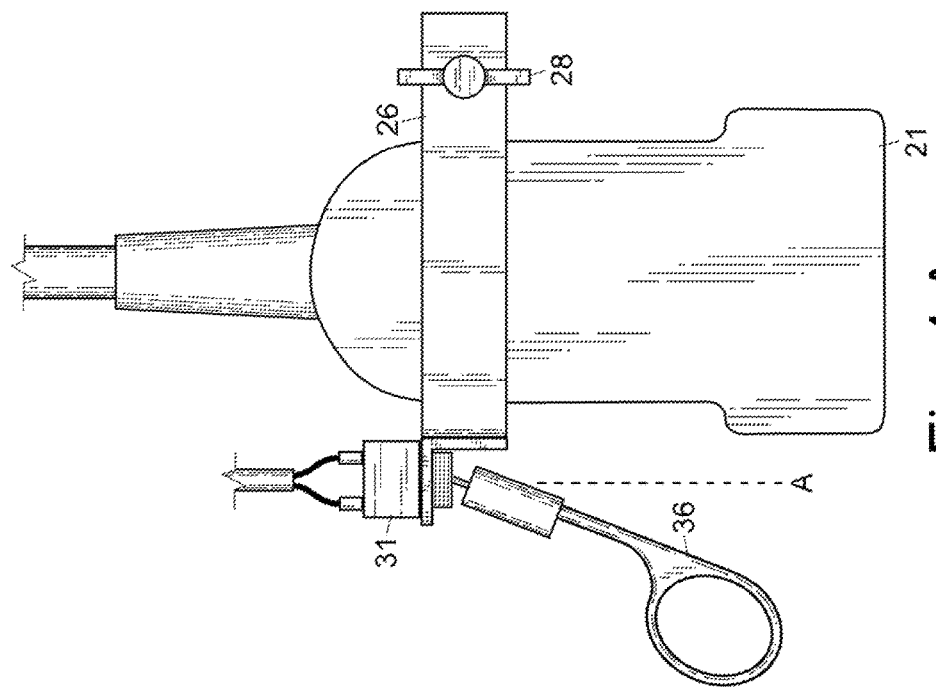

FIG. 3 depicts a perspective view of preferred switch assembly 12 of injection system 10 with various components exploded therefrom. Mount 26 is intended to be frictionally engaged to the exterior surface of probe 21, for example as demonstrated in FIG. 2. In order to facilitate a more secure engagement, preferred mount 26 includes lining 25 positioned along the inner surface of clamp 26. In one embodiment, lining 25 and clamp 26 define complimentary U-shapes, with clamp 26 defining a length slighter greater than that of lining 25. While not intended to be a limitation, lining 25 is preferably formed from a deformable material with a comparatively high coefficient of friction such as polystyrene, neoprene, or the like while clamp 26 is formed from a comparatively more rigid material with a lower coefficient of friction such as a metal or polymeric material. Mount 26 may also include elongated member 27 that preferably defines a plurality of threads at a terminal end opposing winged ears 28, such that the elongated portion of elongated member 27 passes through nut 42 and each of a pair of apertures 29, 29' defined in respective distal ends of clamp 26. Preferably, first aperture 29 is a threaded opening while second aperture 29' is a clearance (i.e. unthreaded) opening, such that elongated member may pass smoothly through second aperture 29' but frictionally and rotatably engages first aperture 29. In this manner the width of clamp 26 can be selectively narrowed as desired, with one hand and without additional tools, to securely engage the exterior surface of probe 21, for example to accommodate the wide and narrow grip orientations described above. One or more additional adjustment members 47 may be included in a preferred embodiment of switch assembly 12, for example an additional elongated member engaged with a threaded hole 48 formed in the "base" of the U-shaped clamp 26. Threaded hole or holes 48 may be positioned at one or both corners of bracket 30 to accommodate wide and narrow grip orientations as described above. This additional feature may further accommodate a secure engagement with a variety of probe 21 shapes and sizes.

Positioned at the opposing longitudinal end from apertures 29, 29', bracket 30 is attached to the exterior surface of clamp 26, for example by welding, adhesive, mechanical fastener, or the like. Bracket 30 is preferably an L-shape defining an opening to receive switch 31 and serves as the connection point for control switch 31 and a plurality of electronic leads, represented with numerals 32, 33, 34, and 35 (for example, indicating start, stop, ground, and reverse signals). Control switch 31 is in mechanical and electronic communication with lever 36 so that any displacement, for example longitudinal or lateral displacement relative to a substantially vertical (i.e. neutral) orientation may be detected and communicated to system control module 20. In the preferred embodiment, switch 31 is characterized as a "momentary" switch, in that it includes a bias to the neutral orientation, such that lever 36 returns to the vertical position unless continuously urged to a different configuration. Lever 36 preferably includes shaft portion 37 and more preferably includes opening 38 that is sized and shaped to receive an anatomy, for example the finger, of a user therethrough. Shaft portion 37 is received within collar 39 that aids in the transmission of lever 36 displacement information to switch via post 40. Fastener 41 ensures that lever 36 has a full range of motion while being affixed to bracket 30, and that recognized displacement events are properly transmitted to system control module 20 for appropriate response. Additional features such as a restraint (not shown) to limit the displacement of lever 36 may also be added as desired.

FIGS. 4A and 4B illustrate elevated side perspective views of lever 36 displaced from the neutral position (vertical axis represented as dotted line "A") in either a first displaced orientation (FIG. 4A) or a second displaced orientation (FIG. 4B). Programmable logic in the form of software (i.e. computer code), hardware (i.e. programmable logic controller or PLC), or firmware stored or accessed by system control module 20 and executed by a processor (not shown) may predetermine that lever 36 in the neutral position (shown generally in FIG. 2) indicates that no action at pump 11 is to be taken. When a user manually urges lever 36 from the neutral position to a first displaced position as illustrated in FIG. 4A, for example by inserting a finger within opening 38 and extending said finger laterally relative to probe 21, system control module 20 initiates a first action. In the context of a nerve block injection, once needle 24 is positioned appropriately, it may be desirable to aspirate prior to the administration of injectate to reduce or prevent the occurrence of an intravascular injection. Therefore, an embodiment of a first action as initiated by system control module 20 is to begin drawing the syringe plunger 18 away from mount 15 to confirm the absence of blood in needle 24 or tubing 43. An embodiment of system control module 20 may continue the first action for a predetermined period of time, but preferably system control module 20 includes logic that terminates the first action when information is detected that lever 36 has returned to the neutral position, which preferably is the default orientation of a momentary switch as described above. Similarly, when a user manually urges lever 36 from the neutral position to a second displaced position as illustrated in FIG. 4B, for example by retracting said finger laterally relative to probe 21, system control module 20 initiates a second action. Again using the nerve block injection as an example, once the lack of blood is confirmed in the method described above, an administration of medicament 14 may take place. Therefore, an embodiment of a second action as initiated by system control module 20 is to drive syringe plunger 18 towards mount 15 to bathe the targeted nerve with an anesthetic solution as is understood in the art. An embodiment of system control module 20 may continue the second action for a predetermined period of time, but preferably system control module 20 includes logic that terminates the second action when information is detected that lever 36 has returned to the neutral position, again the default configuration in the preferred embodiment. Additionally, an embodiment of system control module 20 may detect input from other sources and initiate and/or terminate actions based on this input, independent of or even prioritized over input from lever 36. For example, preferred pump 11 may further include pressure sensor 46 for detecting increases in pressure during an injection or aspiration event (i.e. bidirectional pressure sensitivity). Despite the skill, training, and innovation brought to bear during an injection event, situations may arise whereby the injection needs to be terminated immediately. Beyond even the skilled touch of a physician, such a sensor may detect back-pressure in tubing 43 and send a signal to system control module 20 to halt further injection activity until the source of the pressure is resolved. In one embodiment, pressure sensor 46 may be programmed to detect pressure readings between two and twenty pounds per square inch (2-20 psi) and more preferably between five and fifteen pounds per square inch (5-15 psi). Given that the homeostatic pressure of human tissue is approximate 4 psi, and the homeostatic pressure of nerve tissue is about 15 psi, pressure sensor 46 may be programmed to override inputs from lever 36, preventing any injection event from occurring if excess pressure feedback is detected, for example at about 10 psi. This action may be accompanied by an alert, such as a text message displayed on a monitor or an audio alarm sounded by injection system 10 (not shown).

Figure 5:
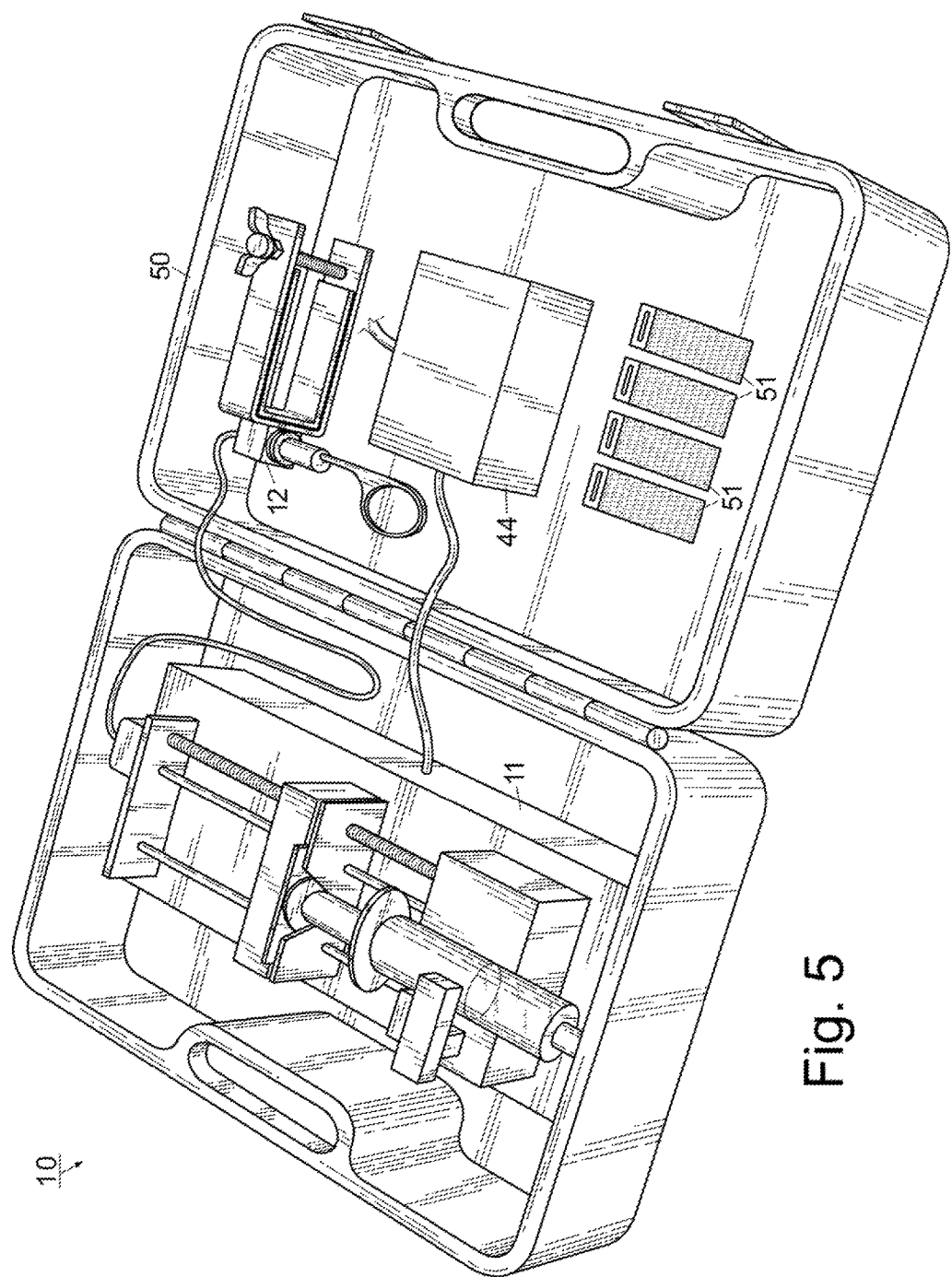
FIG. 5 shows a perspective view of the injection system of FIG. 2 configured for storage or transportation.

FIG. 5 shows a perspective view of the entire injection system 10 stored within carrying case 50 for easy transportation and storage. Unlike prior art solutions to imaging and injection pump systems, injection system 10 is lightweight and mobile, which makes it an ideal solution for healthcare settings where seconds count and a medical provider may not always have the luxury for a large, cumbersome device to be wheeled into a distant examination room or for multiple medical personnel to arrive to facilitate its complicated use.

A method of using injection system 10 to successfully execute a visually-guided injection may include the following steps. Power supply 44 is plugged into an available electrical outlet to provide power to pump 11. The desired volume of medicament is loaded into an appropriate administration vessel such as syringe 13, which is in turn placed into pump 11 with plunger head 17 nestled into receiver 16 and the syringe body held within mount 15, preferably secured in place with rotatable arm 45. Needle 24, hub 22, and tubing 43 are all attached to syringe 13 and probe 21 is positioned within clamp 26 and secured in place, festooning the respective cords, wires, and the like from switch assembly 12 and probe 21 via one or more hook and loop straps 51. Although demonstrated detached in FIG. 5, hook and loop straps 51 are intended to be releaseably affixed to the wire or wires connecting switch 31 to pump 11 and carried by any additional cordage required by the imaging device attached to probe 21, maintaining close proximal distance (i.e. within the width of a user's hand) between prove 21 and lever 36. The imaging device (not shown in its entirety) is initiated and the desired nerve is visualized while needle 24 is manipulated into the appropriate position. After needle 24 is positioned appropriately, the user may engage lever 36 from the neutral position to a first displaced position relative to axis A, for example by extending the finger away from probe 21. This displacement is recognized and communicated by switch 31 to system control module 20 which compels the execution of a first action, for example drawing back on plunger 18 to aspirate needle 24, thereby allowing the user to confirm the absence of blood in needle 24 to prevent an intravascular injection. Lever 36 is returned or returns to the neutral position and the first action is terminated. Lever 36 may then be displaced from the neutral position to a second position relative to axis A, for example by retracting the finger towards probe 21. This displacement is recognized and communicated by switch 31 to system control module 20 which compels the execution of a second action, for example driving forward on plunger 18 to inject the medicament though needle 24, thereby administering the nerve block injection. Lever 36 is thereafter returned or returns to the neutral position and the second action is terminated. The needle 24 may then be removed from the patient and the syringe 13 and tubing 43 connected therewith may be properly disposed of. Probe 21 is released from clamp 26 and pump 11 and switch assembly 12 are properly stowed in case 50 for easy transportation or storage.

The illustrations and examples provided herein are for explanatory purposes and are not intended to limit the scope of the appended claims.

We claim:

1. An injection system comprising a pump connected to a switch assembly, the pump housing a system control module in communication with the switch assembly and the pump, the switch assembly defined by a switch, a mount, a bracket attached to the mount and carrying the switch, and a lever displaceable from a neutral position to a first position and from a neutral position to a second position, the system control module configured to detect the orientation of the lever, wherein detection of the lever in the first position by the system control module engages a predetermined first action by the pump, wherein detection of the lever in the second position by the system control module engages a predetermined second action by the pump, the first action and the second action defined as an aspiration action and an injection action, respectively, wherein the mount is sized and shaped to receive and frictionally engage an exterior surface of an ultrasound transducer probe, and wherein the switch assembly is separate from any control of the ultrasound transducer probe and coupled thereto.

2. The injection system of claim 1 wherein the mount is defined by a clamp.

3. The injection system of claim 2 wherein the clamp defines a U shape.

4. The injection system of claim 1 further comprising a liner, the liner positioned along an interior surface of the clamp so that the liner imparts frictional engagement from the mount to the exterior surface of the ultrasound transducer probe.

5. The injection system of claim 3 wherein the clamp defines a pair of apertures positioned at respective distal ends of the clamp, the apertures sized to receive a first fastener therethrough.

6. The injection system of claim 5 wherein the lever is defined by a loop portion and a shaft portion, the loop portion defining an opening therein.

7. The injection system of claim 6 comprising a second fastener, the second fastener attached to the bracket.

8. The injection system of claim 7 further comprising a post attached to a collar, the lever opposingly attached to the collar relative to the post, the post connected to the second fastener.

9. An injection system for use in the administration of a peripheral nerve block comprising a pump connected to a switch assembly, the pump housing a system control module in communication with the switch assembly and the pump, the switch assembly defined by a switch, a U-shaped clamp mount, a bracket attached to the mount and carrying the switch, and a lever displaceable from a neutral position to a first position and from the neutral position to a second position, the first and second positions defining different orientations, the system control module configured to detect the orientation of the lever, wherein detection of the lever in the first position by the system control module engages a predetermined first action by the pump, wherein detection of the lever in the second position by the system control module engages a predetermined second action by the pump, wherein detection of the lever in the neutral position by the system control module terminates the first and second action by the pump, the first action and the second action defined as an aspiration action and an injection action, respectively, wherein the mount is sized and shaped to receive and frictionally engage an exterior surface of an ultrasound transducer probe, whereby the injection system is engaged by a single medical service provider to simultaneously inject a patient with a medicament with ultrasound guidance, and wherein the switch assembly is separate from any control of the ultrasound transducer probe and coupled thereto.

10. The injection system of claim 9 comprising a sensor housed by the pump, the sensor in communication with the system control module and configured to detect pressure during the pump first or second actions.

11. The injection system of claim 9 further comprising a liner positioned along an interior surface of the clamp so that the liner imparts frictional engagement from the mount to the exterior surface of the ultrasound transducer probe.

12. The injection system of claim 9 wherein the U-shaped clamp defines a pair of apertures positioned at respective distal ends of the clamp, the apertures sized to receive a threaded fastener therethrough.

13. The injection system of claim 10 wherein the lever is defined by a loop portion and a shaft portion, the loop portion defining an opening therein.

14. A method of administering an injection comprising,
providing the injection system of claim 1,
connecting the switch assembly to a probe,
loading an effective amount of medicament into a vessel,
inserting the vessel into the pump, and
displacing the lever from a neutral position to a first position, causing a first action by the pump.

15. The method of claim 14 further comprising,
returning the lever to the neutral position from the first position, and
terminating the first action by the pump.

16. The method of claim 15 further comprising the steps of,
displacing the lever from a neutral position to a second position, causing a second action by the pump,
returning the lever to the neutral position from the second position, and terminating the second action by the pump.

17. A combination injection system and ultrasound transducer probe for use in the administration of a peripheral nerve block, the combination consisting of:
a ultrasound transducer probe defining an exterior surface; and
a pump connected to a switch assembly, the pump housing a system control module in communication with the switch assembly and the pump, the switch assembly defined by a switch, a U-shaped clamp mount, a bracket attached to the mount and carrying the switch, and a lever displaceable from a neutral position to a first position and from the neutral position to a second position, the first and second positions defining different orientations, the system control module configured to detect the orientation of the lever, wherein detection of the lever in the first position by the system control module engages a predetermined first action by the pump, wherein detection of the lever in the second position by the system control module engages a predetermined second action by the pump, wherein detection of the lever in the neutral position by the system control module terminates the first and second action by the pump, the first action and the second action defined as an aspiration action and an injection action, respectively, wherein the mount is sized and shaped to receive and frictionally engage the exterior surface of the ultrasound transducer probe, whereby the injection system is engaged by a single medical service provider to simultaneously inject a patient with a medicament with ultrasound guidance, and wherein the switch assembly is separate from any control of the ultrasound transducer probe and coupled thereto.

18. The combination of claim 17 comprising a sensor housed by the pump, the sensor in communication with the system control module and configured to detect pressure during the pump first or second actions.

19. The combination of claim 17 further comprising a liner positioned along an interior surface of the U-shaped clamp so that the liner imparts frictional engagement from the mount to the exterior surface of the ultrasound transducer probe.

20. The combination of claim 17 wherein the U-shaped clamp defines a pair of apertures positioned at respective distal ends of the clamp, the apertures sized to receive a threaded fastener therethrough.

* * * * *